(12) United States Patent
Howell

(10) Patent No.: US 12,274,836 B2
(45) Date of Patent: Apr. 15, 2025

(54) RAPIDLY INSERTABLE CENTRAL CATHETERS INCLUDING ASSEMBLIES AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 401 days.

(21) Appl. No.: 17/360,694

(22) Filed: Jun. 28, 2021

(65) Prior Publication Data

US 2021/0402149 A1 Dec. 30, 2021

Related U.S. Application Data

(60) Provisional application No. 63/045,599, filed on Jun. 29, 2020.

(51) Int. Cl.
*A61M 25/01* (2006.01)
*A61M 25/00* (2006.01)
(Continued)

(52) U.S. Cl.
CPC .... *A61M 25/0169* (2013.01); *A61M 25/0029* (2013.01); *A61M 25/0097* (2013.01);
(Continued)

(58) Field of Classification Search
CPC .......... A61M 25/0169; A61M 25/0029; A61M 25/0097; A61M 25/0102; A61M 25/0606;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 202012006191 U1 7/2012
EP 0653220 A1 5/1995
(Continued)

OTHER PUBLICATIONS

PCT/US2020/048583 filed Aug. 28, 2020 International Search Report and Written Opinion dated Nov. 13, 2020.
(Continued)

*Primary Examiner* — Nathan R Price
*Assistant Examiner* — Fatimata Sahra Diop
(74) *Attorney, Agent, or Firm* — Rutan & Tucker LLP

(57) ABSTRACT

Disclosed are rapidly insertable central catheters ("RICCs") including assemblies and methods thereof. In some embodiments, a RICC assembly includes a RICC and an introducer. The RICC includes a soft catheter tube having an introducing aperture that opens into a primary lumen of the RICC. The introducer includes an introducer catheter including a hard catheter tube having an introducing hole that opens into a single lumen of the introducer catheter. When the RICC assembly is in a ready-to-deploy state thereof, the introducer catheter is disposed in the primary lumen of the RICC such that a distal end of the introducer catheter extends past a distal end of the RICC. In addition, an introducer needle of the introducer is disposed in the introducer catheter through both the introducing aperture and the introducing hole such that a beveled tip of the introducer needle extends past the distal end of the introducer catheter.

16 Claims, 5 Drawing Sheets

(51) Int. Cl.
*A61M 25/06* (2006.01)
*A61M 25/09* (2006.01)

(52) U.S. Cl.
CPC .... *A61M 25/0102* (2013.01); *A61M 25/0606* (2013.01); *A61M 25/065* (2013.01); *A61M 25/09041* (2013.01); *A61M 2025/0004* (2013.01); *A61M 2025/0037* (2013.01); *A61M 2025/018* (2013.01); *A61M 2025/0183* (2013.01); *A61M 2025/09125* (2013.01)

(58) Field of Classification Search
CPC .......... A61M 25/065; A61M 25/09041; A61M 2025/0004; A61M 2025/0037; A61M 2025/018; A61M 2025/0183; A61M 2025/09125; A61M 25/0662; A61M 25/0026; A61M 25/0043; A61M 25/007; A61M 25/0113; A61M 2210/12
See application file for complete search history.

(56) References Cited

U.S. PATENT DOCUMENTS

| | | | |
|---|---|---|---|
| 3,382,872 | A | 5/1968 | Rubin |
| 3,570,485 | A | 3/1971 | Reilly |
| 3,890,976 | A | 6/1975 | Bazell et al. |
| 4,205,675 | A | 6/1980 | Vaillancourt |
| 4,292,970 | A | 10/1981 | Hession, Jr. |
| 4,468,224 | A | 8/1984 | Enzmann et al. |
| 4,525,157 | A | 6/1985 | Vaillancourt |
| 4,581,019 | A | 4/1986 | Curelaru et al. |
| 4,594,073 | A | 6/1986 | Stine |
| 4,702,735 | A | 10/1987 | Luther et al. |
| 4,743,265 | A | 5/1988 | Whitehouse et al. |
| 4,766,908 | A | 8/1988 | Clement |
| 4,863,432 | A | 9/1989 | Kvalo |
| 4,935,008 | A | 6/1990 | Lewis, Jr. |
| 4,950,252 | A | 8/1990 | Luther et al. |
| 4,994,040 | A | 2/1991 | Cameron et al. |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,115,816 | A | 5/1992 | Lee |
| 5,120,317 | A | 6/1992 | Luther |
| 5,158,544 | A | 10/1992 | Weinstein |
| 5,188,593 | A | 2/1993 | Martin |
| 5,195,962 | A | 3/1993 | Martin et al. |
| 5,207,650 | A | 5/1993 | Martin |
| RE34,416 | E | 10/1993 | Lemieux |
| 5,267,958 | A | 12/1993 | Buchbinder et al. |
| 5,295,970 | A | 3/1994 | Clinton et al. |
| 5,306,247 | A | 4/1994 | Pfenninger |
| 5,312,361 | A | 5/1994 | Zadini et al. |
| 5,322,512 | A | 6/1994 | Mohiuddin |
| 5,328,472 | A | 7/1994 | Steinke et al. |
| 5,350,358 | A | 9/1994 | Martin |
| 5,358,495 | A | 10/1994 | Lynn |
| 5,368,567 | A | 11/1994 | Lee |
| 5,378,230 | A | 1/1995 | Mahurkar |
| 5,380,290 | A | 1/1995 | Makower et al. |
| 5,389,087 | A | 2/1995 | Miraki |
| 5,439,449 | A | 8/1995 | Mapes et al. |
| 5,443,457 | A | 8/1995 | Ginn et al. |
| 5,460,185 | A | 10/1995 | Johnson et al. |
| 5,489,271 | A | 2/1996 | Andersen |
| 5,573,520 | A | 11/1996 | Schwartz et al. |
| 5,683,370 | A | 11/1997 | Luther et al. |
| 5,713,876 | A | 2/1998 | Bogert et al. |
| 5,718,678 | A | 2/1998 | Fleming, III |
| 5,772,636 | A | 6/1998 | Brimhall et al. |
| 5,885,251 | A | 3/1999 | Luther |
| 5,919,164 | A | 7/1999 | Andersen |
| 5,921,971 | A | 7/1999 | Agro et al. |
| 5,947,940 | A | 9/1999 | Beisel |
| 5,957,893 | A | 9/1999 | Luther et al. |
| 5,971,957 | A | 10/1999 | Luther et al. |
| 6,159,198 | A | 12/2000 | Gardeski et al. |
| 6,206,849 | B1 | 3/2001 | Martin et al. |
| 6,228,062 | B1 | 5/2001 | Howell et al. |
| 6,475,187 | B1 | 11/2002 | Gerberding |
| 6,551,284 | B1 | 4/2003 | Greenberg et al. |
| 6,606,515 | B1 | 8/2003 | Windheuser et al. |
| 6,616,630 | B1 | 9/2003 | Woehr et al. |
| 6,626,869 | B1 | 9/2003 | Bint |
| 6,638,252 | B2 | 10/2003 | Moulton et al. |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,991,625 | B1 | 1/2006 | Gately et al. |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,094,222 | B1 | 8/2006 | Siekas et al. |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,976,511 | B2 | 7/2011 | Fojtik |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,361,011 | B2 | 1/2013 | Mendels |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |
| 8,882,713 | B1 | 11/2014 | Call et al. |
| 8,900,192 | B2 | 12/2014 | Anderson et al. |
| 8,900,207 | B2 | 12/2014 | Uretsky |
| 8,915,884 | B2 | 12/2014 | Tal et al. |
| 8,956,327 | B2 | 2/2015 | Bierman et al. |
| 9,023,093 | B2 | 5/2015 | Pal |
| 9,067,023 | B2 | 6/2015 | Bertocci |
| 9,126,012 | B2 | 9/2015 | McKinnon et al. |
| 9,138,252 | B2 | 9/2015 | Bierman et al. |
| 9,180,275 | B2 | 11/2015 | Helm |
| 9,265,920 | B2 | 2/2016 | Rundquist et al. |
| 9,272,121 | B2 | 3/2016 | Piccagli |
| 9,445,734 | B2 | 9/2016 | Grunwald |
| 9,522,254 | B2 | 12/2016 | Belson |

(56) References Cited

U.S. PATENT DOCUMENTS

| | | |
|---|---|---|
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,688,281 B2 | 6/2020 | Blanchard et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,400,260 B2 | 8/2022 | Huang et al. |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1* | 11/2005 | Elkins ............... A61M 25/0068 604/239 |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0190778 A1 | 8/2011 | Arpasi et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1* | 7/2014 | Belson ............... A61M 25/0606 604/510 |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1* | 8/2016 | Mitchell ........... A61M 25/0029 |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0331938 A1 | 11/2016 | Blanchard et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |

(56) References Cited

U.S. PATENT DOCUMENTS

| | | |
|---|---|---|
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1 | 11/2019 | Ribelin et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0062596 A1 | 3/2022 | Ribelin et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331562 A1 | 10/2022 | Jaros et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1 | 6/2023 | Parikh et al. |
| 2023/0233814 A1 | 7/2023 | Howell et al. |
| 2023/0381459 A1 | 11/2023 | Belson et al. |
| 2024/0009427 A1 | 1/2024 | Howell et al. |
| 2024/0050706 A1 | 2/2024 | Howell et al. |
| 2024/0198058 A1 | 6/2024 | Howell et al. |
| 2025/0001136 A1 | 1/2025 | Mitchell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 9857685 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |

(56) References Cited

FOREIGN PATENT DOCUMENTS

| | | |
|---|---|---|
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021038041 A1 | 3/2021 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2021226050 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |
| WO | 2022/217098 A1 | 10/2022 |
| WO | 2023014994 A1 | 2/2023 |
| WO | 2023049498 A1 | 3/2023 |
| WO | 2023049505 A1 | 3/2023 |
| WO | 2023049511 A1 | 3/2023 |
| WO | 2023049519 A1 | 3/2023 |
| WO | 2023049522 A1 | 3/2023 |
| WO | 2023146792 A1 | 8/2023 |

OTHER PUBLICATIONS

PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 17/031,478, filed Sep. 24, 2020 Non-Final Office Action dated May 11, 2022.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 16/398,020, filed Apr. 29, 2019 Final Office Action dated Jan. 25, 2022.
U.S. Appl. No. 17/077,728, filed Oct. 22, 2020 Non-Final Office Action dated Feb. 9, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.

(56) References Cited

OTHER PUBLICATIONS

U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
U.S. Appl. No. 16/398,020, filed Apr. 29, 2019 Board Decision dated Oct. 30, 2023.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/358,504, filed Jun. 25, 2021 Non-Final Office Action dated Oct. 4, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Restriction Requirement dated Oct. 3, 2023.
U.S. Appl. No. 17/557,924, filed Dec. 21, 2021 Non-Final Office Action dated Nov. 3, 2023.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 16/398,020, filed Apr. 29, 2019 Non-Final Office Action dated Jan. 18, 2024.
U.S. Appl. No. 17/234,611, filed Apr. 19, 2021 Non-Final Office Action dated Apr. 23, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/358,504, filed Jun. 25, 2021 Final Office Action dated Mar. 13, 2024.
U.S. Appl. No. 17/390,682, filed Jul. 30, 2021 Final Office Action dated May 6, 2024.
U.S. Appl. No. 17/392,061, filed Aug. 2, 2021 Advisory Action dated Feb. 14, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Non-Final Office Action dated Jan. 9, 2024.
U.S. Appl. No. 17/554,978, filed Dec. 17, 2021 Non-Final Office Action dated Apr. 19, 2024.
U.S. Appl. No. 17/557,924, filed Dec. 21, 2021 Final Office Action dated Feb. 29, 2024.
U.S. Appl. No. 16/398,020, filed Apr. 29, 2019 Notice of Allowance dated May 20, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Notice of Allowance dated Jul. 17, 2024.
U.S. Appl. No. 17/390,682, filed Jul. 30, 2021 Non-Final Office Action dated Jul. 5, 2024.
U.S. Appl. No. 17/513,789, filed Oct. 28, 2021 Final Office Action dated Jul. 9, 2024.
U.S. Appl. No. 17/554,978, filed Dec. 17, 2021 Notice of Allowance dated Jul. 24, 2024.
U.S. Appl. No. 17/392,061, filed Aug. 2, 2021 Final Office Action dated Jan. 2, 2025.
U.S. Appl. No. 17/461,619, filed Aug. 30, 2021 Restriction Requirement dated Dec. 6, 2024.
U.S. Appl. No. 17/513,789, filed Oct. 28, 2021 Notice of Allowance dated Jan. 3, 2025.
U.S. Appl. No. 17/557,924, filed Dec. 21, 2021 Notice of Allowance dated Dec. 11, 2024.

* cited by examiner

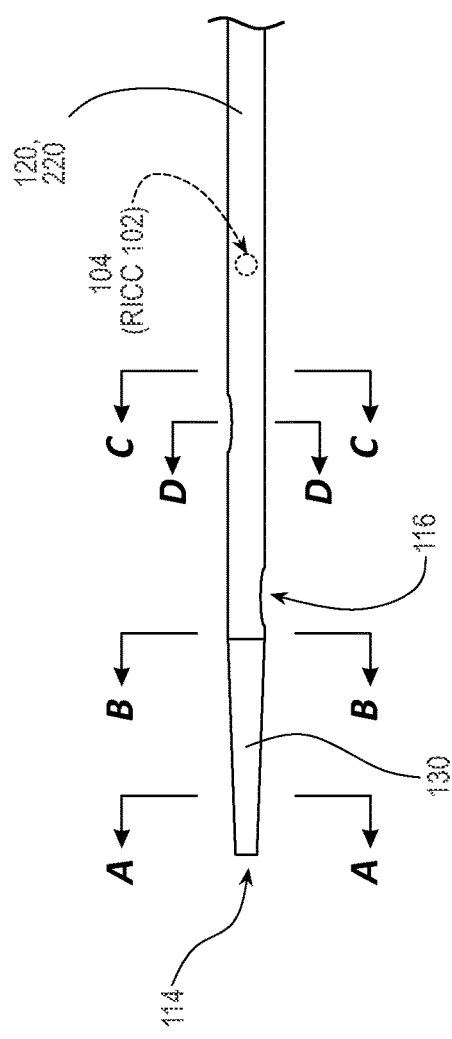
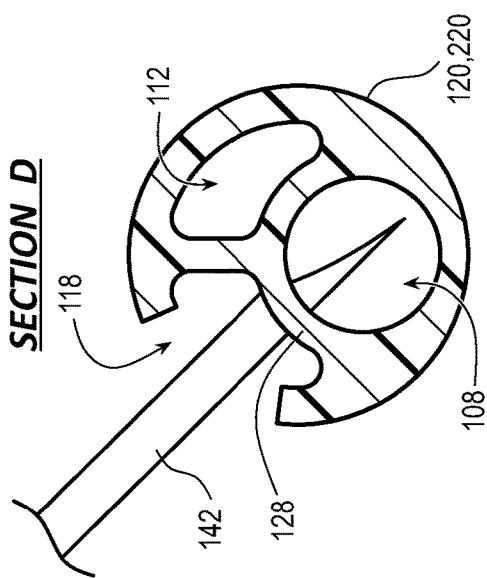
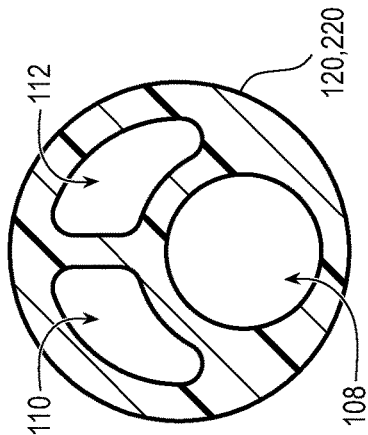
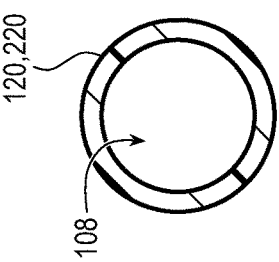
FIG. 4
FIG. 5 SECTION A
FIG. 6 SECTION B OR C
FIG. 7 SECTION D

RAPIDLY INSERTABLE CENTRAL CATHETERS INCLUDING ASSEMBLIES AND METHODS THEREOF

PRIORITY

This application claims the benefit of priority to U.S. Provisional Application No. 63/045,599, filed Jun. 29, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing.

SUMMARY

Disclosed herein is a RICC assembly including, in some embodiments, a RICC and an introducer. The RICC includes a soft catheter tube, a catheter hub, and one or more extension legs. The soft catheter tube has an introducing aperture through a side of the soft catheter tube in a distal-end portion of the soft catheter tube. The introducing aperture opens into an introducing portion of a primary lumen of the RICC, which portion extends from the introducing aperture to a distal end of the RICC. The catheter hub is coupled to a proximal-end portion of the soft catheter tube. Each extension leg of the one-or-more extension legs is coupled to the catheter hub by a distal-end portion of the extension leg. The introducer includes an introducer catheter and an introducer needle. The introducer catheter includes a hard catheter tube having an introducing hole through a side of the hard catheter tube in a distal-end portion of the hard catheter tube. The introducing hole opens into an introducing portion of a single lumen of the introducer catheter, which portion extends from the introducing hole to a distal end of the introducer catheter. The introducer catheter is disposed in the primary lumen of the RICC such that the distal end of the introducer catheter extends past the distal end of the RICC when the RICC assembly is in a ready-to-deploy state of the RICC assembly. In addition, the introducer needle is disposed in the introducer catheter through both the introducing aperture and the introducing hole such that a beveled tip in a distal-end portion of the introducer needle extends past the distal end of the introducer catheter.

In some embodiments, the RICC assembly further includes an access guidewire. The access guidewire is disposed in the introducer needle such that a distal end of the access guidewire is proximal of the beveled tip but distal of the distal end of the RICC when the RICC assembly is in the ready-to-deploy state.

In some embodiments, the access guidewire includes a stop about a proximal-end portion of the access guidewire forming a stop end of the access guidewire. The stop end of the access guidewire is configured to provide a distal limit for advancing the access guidewire into the RICC.

In some embodiments, the RICC assembly further includes a maneuver guidewire. The maneuver guidewire is disposed in the introducer catheter such that a distal end of the maneuver guidewire is proximal of the introducing hole but distal of the catheter hub when the RICC assembly is in the ready-to-deploy state.

In some embodiments, the maneuver guidewire includes a stop about a proximal-end portion of the maneuver guidewire forming a stop end of the maneuver guidewire. The stop end of the maneuver guidewire is configured to provide a distal limit for advancing the maneuver guidewire into the RICC.

In some embodiments, the soft catheter tube is formed of a first material having a first durometer and the hard catheter tube is formed of a second material having a second durometer. The second durometer is greater than the first durometer, which provides the RICC assembly a column strength for advancing the RICC into a blood-vessel lumen over a guidewire.

In some embodiments, the RICC includes a set of three lumens. The set of three lumens includes the primary lumen, a secondary lumen, and a tertiary lumen formed of fluidly connected portions of three catheter-tube lumens, three hub lumens, and three extension-leg lumens.

In some embodiments, the primary lumen has a primary-lumen aperture in the distal end of the RICC. The secondary lumen has a secondary-lumen aperture in the side of the soft catheter tube proximal of the primary-lumen aperture. The tertiary lumen has a tertiary-lumen aperture in the side of the soft catheter tube proximal of the secondary-lumen aperture but distal of the introducing aperture.

Also disclosed herein is a RICC assembly including, in some embodiments, a RICC and an introducer. The RICC includes a soft catheter tube, a catheter hub, and one or more extension legs. The soft catheter tube has a primary-lumen aperture in a distal end of the soft catheter tube and a secondary-lumen aperture in a side of the soft catheter tube in a distal-end portion of the soft catheter tube. The catheter hub is coupled to a proximal-end portion of the soft catheter tube. Each extension leg of the one-or-more extension legs is coupled to the catheter hub by a distal-end portion of the extension leg. The introducer includes an introducer catheter and an introducer needle. The introducer catheter includes a hard catheter tube having an introducing hole through a side of the hard catheter tube in a distal-end portion of the hard catheter tube. The introducer catheter is disposed in a primary lumen of the RICC such that a distal end of the introducer catheter extends past a distal end of the RICC when the RICC assembly is in a ready-to-deploy state of the RICC assembly. In addition, the introducer needle is disposed in the introducer catheter through a combination of the secondary-lumen aperture, a septum dividing a secondary lumen from the primary lumen, and the introducing hole. Disposed as such, a beveled tip in a distal-end portion of the introducer needle extends past the distal end of the introducer catheter when the RICC assembly is in the ready-to-deploy state.

In some embodiments, the RICC assembly further includes an access guidewire. The access guidewire is disposed in the introducer needle such that a distal end of the access guidewire is proximal of the beveled tip but distal of the distal end of the RICC when the RICC assembly is in the ready-to-deploy state.

In some embodiments, the access guidewire includes a stop about a proximal-end portion of the access guidewire forming a stop end of the access guidewire. The stop end of the access guidewire is configured to provide a distal limit for advancing the access guidewire into the RICC.

In some embodiments, the RICC assembly further includes a maneuver guidewire. The maneuver guidewire is disposed in the introducer catheter such that a distal end of the maneuver guidewire is proximal of the introducing hole but distal of the catheter hub when the RICC assembly is in the ready-to-deploy state.

In some embodiments, the maneuver guidewire includes a stop about a proximal-end portion of the maneuver guidewire forming a stop end of the maneuver guidewire. The stop end of the maneuver guidewire is configured to provide a distal limit for advancing the maneuver guidewire into the RICC.

In some embodiments, the soft catheter tube is formed of a first material having a first durometer and the hard catheter tube is formed of a second material having a second durometer. The second durometer is greater than the first durometer, which provides the RICC assembly a column strength for advancing the RICC into a blood-vessel lumen over a guidewire.

In some embodiments, the RICC includes a set of three lumens. The set of three lumens includes the primary lumen, the secondary lumen, and a tertiary lumen formed of fluidly connected portions of three catheter-tube lumens, three hub lumens, and three extension-leg lumens.

In some embodiments, the primary lumen has the primary-lumen aperture in the distal end of the RICC. The secondary lumen has the secondary-lumen aperture in the side of the soft catheter tube proximal of the primary-lumen aperture. The tertiary lumen has a tertiary-lumen aperture in the side of the soft catheter tube proximal of the secondary-lumen aperture.

Also disclosed is a method for using a RICC assembly. The method includes, in some embodiments, an RICC assembly-obtaining step, a needle tract-establishing step, an access guidewire-advancing step, and an introducer needle-withdrawing step. The RICC assembly-obtaining step includes obtaining a RICC assembly including the RICC and an introducer. The introducer includes an introducer catheter disposed in a primary lumen of the RICC such that a distal-end portion of the introducer catheter extends past a distal end of the RICC. The needle tract-establishing step includes establishing a needle tract from an area of skin to a blood-vessel lumen of a patient with a beveled tip of an introducer needle of the introducer. The introducer needle extends through a side of a soft catheter tube of the RICC, through a side of a hard catheter tube of the introducer catheter, and out the distal end of the introducer catheter. The access guidewire-advancing step includes advancing an access guidewire through the introducer needle and into the blood-vessel lumen of the patient. The introducer needle-withdrawing step includes withdrawing the introducer needle from both the blood-vessel lumen and the RICC assembly leaving the access guidewire and the introducer catheter in the blood-vessel lumen.

In some embodiments, the method further includes an ensuring step of ensuring the distal end of the introducer catheter extends at least about 1-7 cm beyond the distal end of the RICC before performing the needle tract-establishing step.

In some embodiments, the method further includes a first RICC-advancing step of advancing the distal-end portion of the introducer catheter into the blood-vessel lumen over the access guidewire.

In some embodiments, the method further includes a maneuver guidewire-advancing step of advancing a maneuver guidewire through the introducer catheter and into the blood-vessel lumen.

In some embodiments, the maneuver guidewire-advancing step requires first withdrawing the introducer needle from both the blood-vessel lumen and the RICC assembly.

In some embodiments, the method further includes a second RICC-advancing step of advancing both the distal-end portion of the introducer catheter and a distal-end portion of the RICC farther into the blood-vessel lumen over the maneuver guidewire.

These and other features of the concepts provided herein will become more apparent to those of skill in the art in view of the accompanying drawings and following description, which describe particular embodiments of such concepts in greater detail.

DRAWINGS

FIG. 4 illustrates a distal-end portion of a soft catheter tube of the RICC of FIG. 1 or 2 in accordance with some embodiments.

FIG. 5 illustrates a first transverse cross section of the soft catheter tube in accordance with some embodiments.

FIG. 6 illustrates a second or third transverse cross section of the soft catheter tube in accordance with some embodiments.

FIG. 7 illustrates a fourth transverse cross section of the soft catheter tube with an introducer needle through septum thereof in accordance with some embodiments.

DESCRIPTION

Figure 1:
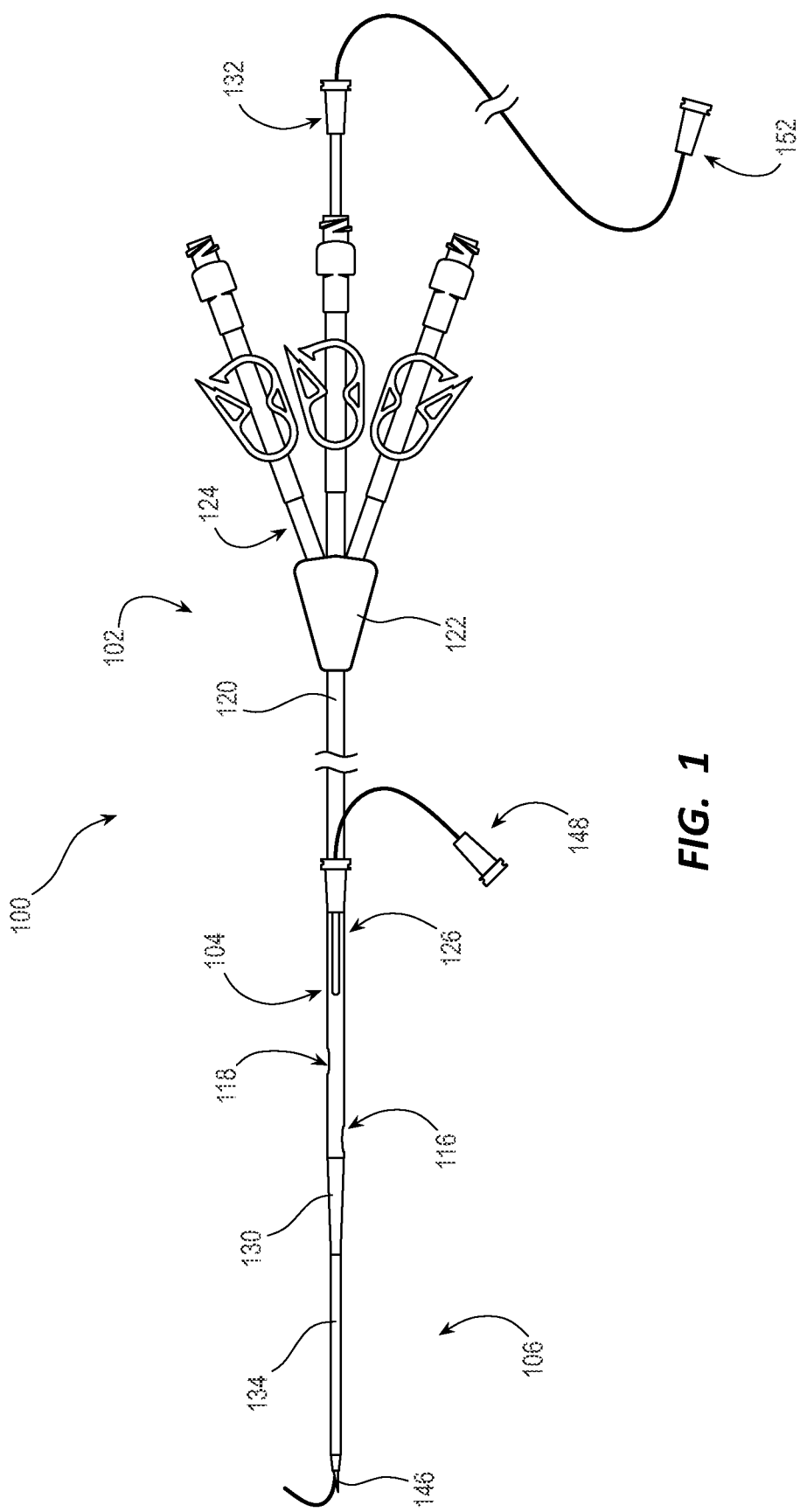
FIG. 1 illustrates a RICC assembly with a RICC including an introducing aperture in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof. Disclosed herein are RICCs including catheter assemblies and methods thereof that address the foregoing.

Figure 2:
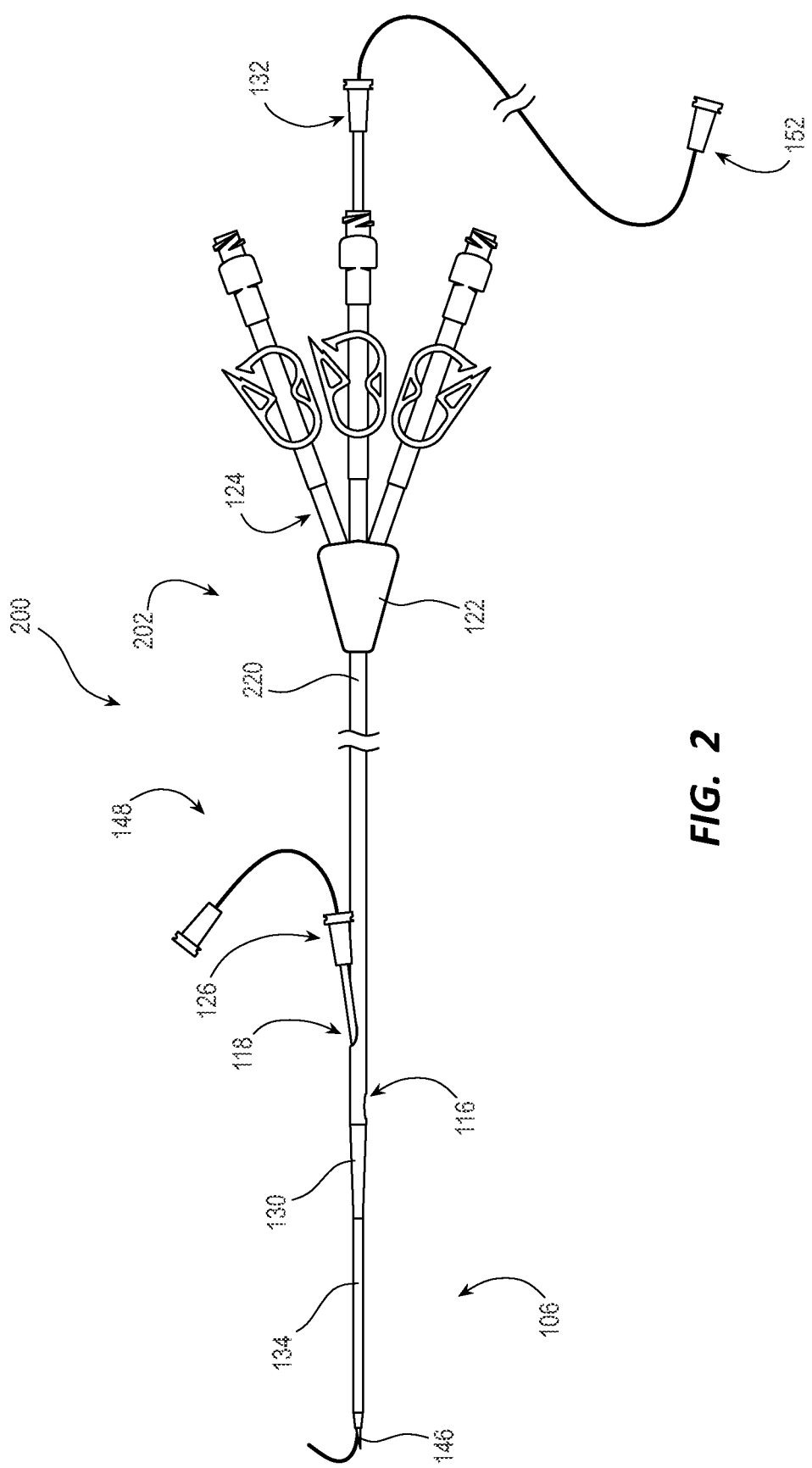
FIG. 2 illustrates a RICC assembly with a RICC lacking the introducing aperture in accordance with some embodiments.

FIG. 1 illustrates a RICC assembly 100 with a RICC 102 including an introducing aperture 104 in accordance with some embodiments. FIG. 2 illustrates a RICC assembly 200 with a RICC 202 lacking the introducing aperture 104 in accordance with some embodiments.

As shown, the RICC assembly 100 or 200 includes the RICC 102 or 202 and an introducer 106 coupled together in a ready-to-deploy state of the RICC assembly 100 or 200. The RICCs 102 and 202 and the introducer 106 are described, in turn, in sections set forth below; however, some crossover between the sections for the RICCs 102 and 202 and the introducer 106 exist in view of the interrelatedness of the RICCs 102 and 202 and the introducer 106 in the RICC assemblies 100 and 200.

The RICC 102 differs from the RICC 202 with respect to a presence of the introducing aperture 104 in the RICC 102, which introducing aperture 104 is dedicated to accommodating insertion of the introducer needle 126 of the introducer 106 therethrough for coupling the RICC 102 and the introducer 106 together in the RICC assembly 100. The RICC 202 lacks such a dedicated introducing aperture 104, thereby requiring a different mode of coupling the RICC 202 and the introducer 106 together in the RICC assembly 200 than in the RICC assembly 100.

The RICC 102 or 202 can be a monoluminal or multiluminal RICC (e.g., a diluminal RICC, a triluminal RICC, a tetraluminal RICC, a pentaluminal RICC, a hexaluminal RICC, etc.). For example, the RICC 202, which lacks the introducing aperture 104, can be monoluminal. Such a RICC also lacks the secondary-lumen aperture 116 and the tertiary-lumen aperture 118 set forth below. In another example, the RICC 102 or 202 can be multiluminal. As shown in FIG. 1 or 2, the RICC 102 or 202 is triluminal including a set of three lumens. Such a set of three lumens includes a primary lumen 108 (e.g., a distal lumen), a secondary lumen 110 (e.g., a medial lumen), and a tertiary lumen 112 (e.g., a proximal lumen) formed of fluidly connected portions of three catheter-tube lumens, three hub lumens, and three extension-leg lumens. (See FIGS. 4-7.)

Whether the RICC 102 or 202 is monoluminal or multiluminal, the RICC 102 or 202 includes at least the primary lumen 108. The primary lumen 108 typically extends from a proximal end of the RICC 102 or 202 to a distal end of the RICC 102 or 202 such as from an opening of a corresponding Luer connector to a primary-lumen aperture 114 in a distal end of the soft catheter tube 120 or 220 set forth below. When the RICC 102 or 202 has two or more lumens, the RICC 102 or 202 further includes at least the secondary lumen 110. The secondary lumen 110 typically extends from the proximal end of the RICC 102 or 202 to a distal-end portion of the RICC 102 or 202 such as from an opening of a corresponding Luer connector to a secondary-lumen aperture 116 in the distal-end portion of the soft catheter tube 120 or 220 proximal of the primary-lumen aperture 114. When the RICC 102 or 202 has three or more lumens, the RICC 102 or 202 further includes at least the tertiary lumen 112. The tertiary lumen 112 typically extends from the proximal end of the RICC 102 or 202 to the distal-end portion of the RICC 102 or 202 such as from an opening of a corresponding Luer connector to a tertiary-lumen aperture 118 in the distal-end portion of the soft catheter tube 120 or 220 proximal of the secondary-lumen aperture 116. Notwithstanding the foregoing, each lumen of the secondary lumen 110 and the tertiary lumen 112 can distally extend slightly farther than the secondary-lumen aperture 116 and the tertiary-lumen aperture 118, respectively, in view of different manufacturing methods. (See FIGS. 4 and 6.)

Whether the RICC 102 or 202 includes the introducing aperture 104 or not, the RICC 102 or 202 further includes an introducing lumen coincident with a distal-end portion of the primary lumen 108. In other words, the introducing lumen is an introducing portion of the primary lumen 108 of the RICC 102 or 202. In the RICC 102, the introducing lumen is the distal-end portion of the primary lumen 108 extending from the introducing aperture 104 to the primary-lumen aperture 114. The introducing aperture 104, which can be distal of the secondary-lumen aperture 116, between the secondary-lumen aperture 116 and the tertiary-lumen aperture 118, or proximal of the tertiary-lumen aperture 118, opens directly into a proximal end of the introducing portion of the primary lumen 108 of the RICC 102. In the RICC 202, the introducing lumen is the distal-end portion of the primary lumen 108 extending from either the secondary-lumen aperture 116 or the tertiary-lumen aperture 118 to the primary-lumen aperture 114. Whether the introducing lumen extends from the secondary-lumen aperture 116 or the tertiary-lumen aperture 118 depends upon which aperture of the foregoing apertures accommodates the introducer needle 126 of the introducer 106. Neither the secondary-lumen aperture 116 nor the tertiary-lumen aperture 118 opens directly into a proximal end of the introducing portion of the primary lumen 108 of the RICC 202. Instead, the introducer needle 126 pierces the septum 128 between the secondary lumen 110 or the tertiary lumen 112 and the primary lumen 108 respectively by way of the secondary-lumen aperture 116 or the tertiary-lumen aperture 118.

The RICC 102 or 202 includes a soft catheter tube 120 or 220, a catheter hub 122, and one or more extension legs 124.

FIG. 4 illustrates a distal-end portion of the soft catheter tube 120 or 220 of the RICC 102 or 202 of FIG. 1 or 2 in accordance with some embodiments. FIGS. 5-7 illustrate various transverse cross sections of the soft catheter tube 120 or 220 in accordance with some embodiments. FIG. 7 further illustrates an introducer needle 126 through a septum 128 of the catheter tube 220 in accordance with some embodiments.

The soft catheter tube 120 or 220 includes a distal tip 130 in a distal-end portion of the soft catheter tube 120 or 220 corresponding to the distal end of the RICC 102 or 202. Like that set forth above for the RICCs 102 and 202, the soft catheter tube 120 or 220 can be monoluminal or multiluminal. Indeed, the soft catheter tube 120 or 220 includes one or more catheter-tube lumens corresponding in name and number to those of the RICC 102 or 202. The one-or-more catheter-tube lumens extend through the soft catheter tube 120 or 220 as set forth above for the RICC 102 or 202.

The soft catheter tube 120 differs from the soft catheter tube 220 with respect to a presence of the introducing aperture 104 through a side of the soft catheter tube 120 in the distal-end portion thereof. Again, the introducing aperture 104 is dedicated to accommodating insertion of the introducer needle 126 of the introducer 106 therethrough for coupling the RICC 102 and the introducer 106 together in the RICC assembly 100. The soft catheter tube 220 lacks such a dedicated introducing aperture 104, thereby requiring a different mode of coupling the RICC 202 and the introducer 106 together in the RICC assembly 200 than in the RICC assembly 100.

Notwithstanding the foregoing, the soft catheter tube 120 or 220 can include n−1 side apertures through the side of the soft catheter tube 120 or 220 in accordance with a number of lumens n of the RICC 102 or 202. Indeed, in consideration of the RICC 102 or 202 set forth above having three lumens, the soft catheter tube 120 or 220 can include two side apertures including the secondary-lumen aperture 116 in the side of the soft catheter tube 120 or 220 proximal of the primary-lumen aperture 114 and the tertiary-lumen aperture 118 in the side of the soft catheter tube 120 or 220 proximal of the secondary-lumen aperture 116. In addition to providing different apertures for aspirating blood, delivering fluids, or the like, such side apertures are important for establishing an introducing lumen for introducing RICCs such as the RICC 202.

The catheter hub 122 is coupled to a proximal-end portion of the soft catheter tube 120 or 220. The catheter hub 122 includes one or more catheter-hub lumens corresponding in number to the one-or-more catheter-tube lumens. The one-or-more catheter-hub lumens extend through an entirety of the catheter hub 122 from a proximal end of the catheter hub 122 to a distal end of the catheter hub 122.

Each extension leg of the one-or-more extension legs 124 is coupled to the catheter hub 122 by a distal-end portion of the extension leg. The one-or-more extension legs 124 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 124 typically includes a Luer connector coupled to the extension leg, through which Luer connector the extension leg and the extension-leg lumen thereof can be connected to another medical device.

The introducer 106 includes an introducer catheter 132 and the introducer needle 126.

The introducer catheter 132 includes a hard catheter tube 134, an introducer-catheter hub 136 about a proximal-end portion of the hard catheter tube 134, and a distal tip 138 in a distal-end portion of the hard catheter tube 134.

The introducer catheter 132 also includes an introducing hole 140 through a side of the hard catheter tube 134 in the distal-end portion thereof. The introducing hole 140 opens into an introducing portion of a single lumen of the introducer catheter 132, which introducing portion extends from the introducing hole 140 to a distal end of the introducer catheter 132. When the RICC assembly 100 or 200 is in the ready-to-deploy state, the introducer catheter 132 is disposed in the primary lumen 108 of the RICC 102 or 202 such that the distal end of the introducer catheter 132 extends at least about 1-7 cm beyond the distal end of the RICC 102 or 202, which is useful for dilation of tissue with the distal-end portion of the introducer catheter 132 or the hard catheter tube 134 thereof.

With respect to the soft catheter tube 120 or 220 of the RICC 102 or 202 and the hard catheter tube 134 of the introducer catheter 132, the soft catheter tube 120 or 220 is formed of a first material having a first durometer and the hard catheter tube 134 is formed of a second material having a second durometer. The first durometer is less than the second durometer, thereby making the soft catheter tube 120 or 220 relatively softer than the hard catheter tube 134. In other words, the second durometer is greater than the first durometer, thereby making the hard catheter tube 134 relatively harder than the soft catheter tube 120 or 220. The hard catheter tube 134 provides the RICC assembly 100 or 200 a column strength for advancing the RICC 102 or 202 into a blood-vessel lumen over a guidewire such as the maneuver guidewire 152 set forth below.

It should be understood the first durometer and the second durometer can be on different scales (e.g., Type A or Type D), so the first durometer of the first polymeric material might not be numerically less than the second durometer of the second polymeric material. Likewise, the second durometer of the second polymeric material might not be numerically greater than the first durometer of the first polymeric material in view of the different scales. That said, the hardness of the first polymeric material can still be less than the hardness of the second polymeric material or the hardness of the second polymeric material can still be greater than the hardness of the first polymeric material because the different scales, each of which ranges from 0 to 100, are designed for characterizing different materials in groups of the materials having a like hardness.

Notwithstanding the foregoing, the soft catheter tube 120 or 220 and the hard catheter tube 134 can be formed of a same polymeric material or different polymeric materials having substantially equal durometers provided a column strength of the soft catheter tube 120 or 220 in combination with the hard catheter tube 134 is sufficient to prevent buckling of the soft catheter tube 120 or 220 when inserted into an insertion site and advanced through a vasculature of a patient.

The introducer needle 126 includes a shaft 142, an introducer-needle hub 144 about a proximal-end portion of the shaft 142, and a beveled tip 146 in a distal-end portion of the shaft 142.

When the RICC assembly 100 is in the ready-to-deploy state, the introducer needle 126 or the shaft 142 thereof is disposed in the single lumen of the introducer catheter 132 through a combination of the introducing aperture 104 of the RICC 102 or the soft catheter tube 120 thereof and the introducing hole 140 of the introducer catheter 132 or the hard catheter tube 134 thereof such that the beveled tip 146 of the introducer needle 126 extends past the distal end of the introducer catheter 132 for establishing a percutaneous puncture. However, when the RICC assembly 200 is in the ready-to-deploy state, the introducer needle 126 or the shaft 142 thereof is disposed in the single lumen of the introducer catheter 132 through a combination of the secondary-lumen aperture 116 or the tertiary-lumen aperture 118 of the RICC 202 or the soft catheter tube 220 thereof, the septum 128 dividing the secondary lumen 110 or tertiary lumen 112 from the primary lumen 108 of the RICC 202 or the soft catheter tube 220 thereof, and the introducing hole 140 of the introducer catheter 132 or the hard catheter tube 134 thereof. Disposed as such, the beveled tip 146 in the distal-end portion of the introducer needle 126 extends past the distal end of the introducer catheter 132 when the RICC assembly 100 or 200 is in the ready-to-deploy state.

The RICC assembly 100 or 200 further includes an access guidewire 148.

When the RICC assembly 100 or 200 is in at least the ready-to-deploy state, the access guidewire 148 is disposed in a needle lumen of the introducer needle 126 such that a distal end of the access guidewire 148 is proximal of the beveled tip 146 of the introducer needle 126 but distal of the distal end of the RICC 102 or 202, which allows for immediate advancement of the distal end of the access guidewire 148 beyond the beveled tip 146 of introducer needle 126 and into a blood-vessel lumen upon establishing access thereto.

The access guidewire 148 includes a stop (e.g., a hub, a ball, a slug, etc.) about a proximal-end portion of the access guidewire 148 forming a stop end 150 (e.g., a hub end, a ball end, a slug end, etc.) of the access guidewire 148. The stop end 150 of the access guidewire 148 is larger than any aperture of the RICC 102 or 202 or the soft catheter tube 120 or 220 thereof, thereby providing a distal limit for advancing the access guidewire 148 into the RICC 102 or 202.

Figure 3:
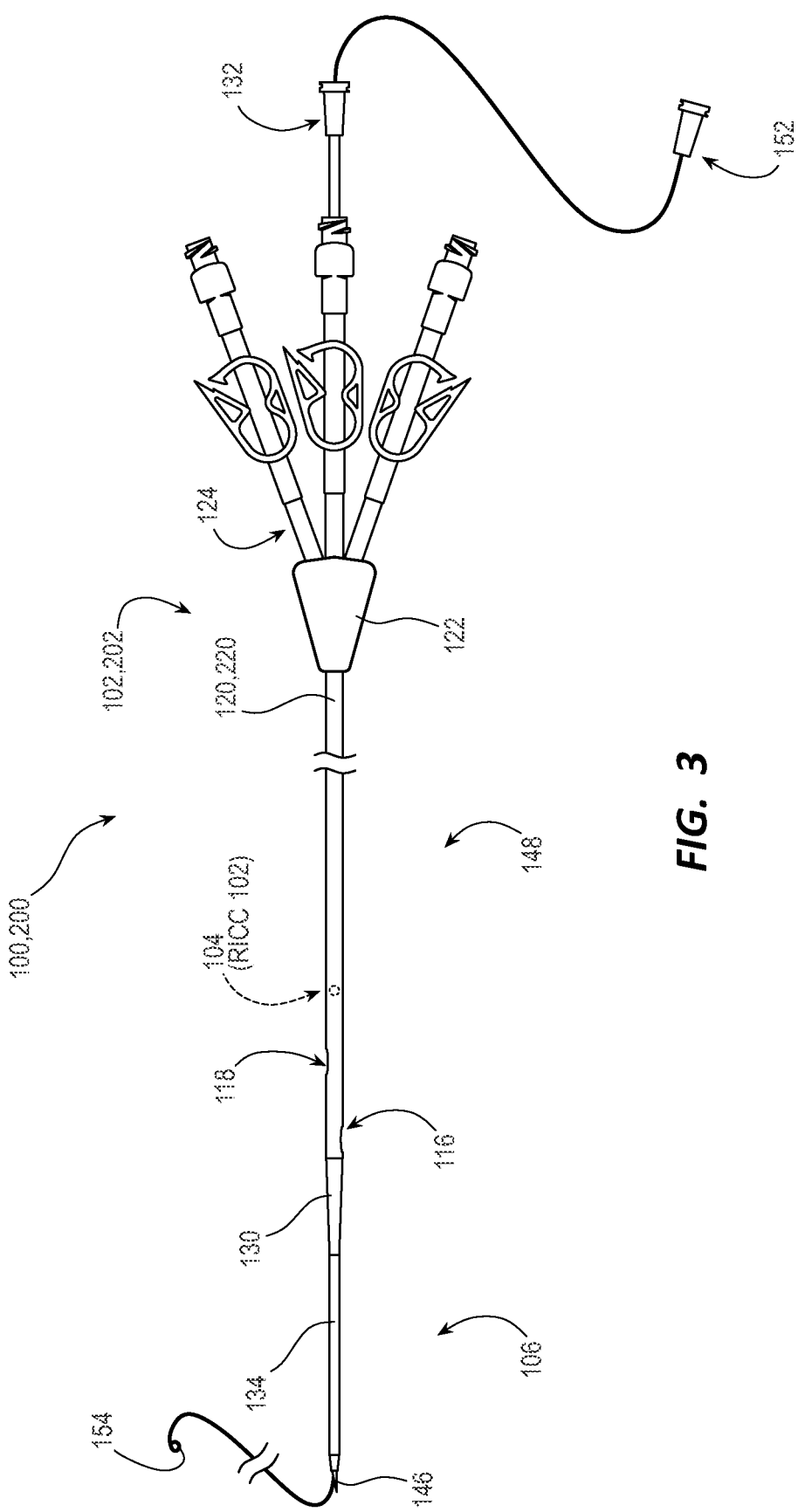
FIG. 3 illustrates the RICC assembly of FIG. 1 or 2 with a maneuver guidewire therethrough in accordance with some embodiments.

FIG. 3 illustrates the RICC assembly 100 or 200 with a maneuver guidewire 152 therethrough in accordance with some embodiments.

The RICC assembly 100 or 200 further includes a maneuver guidewire 152 including an atraumatic tip 154 (e.g., a coiled or partially coiled tip) and a length sufficient for advancing the maneuver guidewire 152 to the lower ⅓ of the superior vena cava ("SVC") of the heart.

When the RICC assembly 100 or 200 is in at least the ready-to-deploy state, the maneuver guidewire 152 is disposed in the single lumen of the introducer catheter 132 such that a distal end of the maneuver guidewire 152 is proximal of the introducing hole 140 but distal of the catheter hub 122, which allows for immediate advancement of the distal end of the maneuver guidewire 152 into the blood-vessel lumen upon removing the introducer needle 126 or the shaft 142 thereof from the single lumen of the introducer catheter 132. Indeed, the maneuver guidewire 152 cannot be distally advanced farther into the single lumen of the introducer catheter 132 due the presence of the introducer needle 126 or the shaft 142 thereof in at least the ready-to-deploy state of the RICC assembly 100 or 200.

The maneuver guidewire 152 includes a stop (e.g., a hub, a ball, a slug, etc.) about a proximal-end portion of the maneuver guidewire 152 forming a stop end 156 (e.g., a hub end, a ball end, a slug end, etc.) of the maneuver guidewire 152. The stop end 156 of the maneuver guidewire 152 is larger than a proximal-end opening in the introducer-catheter hub 136, thereby providing a distal limit for advancing the maneuver guidewire 152 into the RICC 102 or 202.

Methods

Methods of the RICC assembly 100 or 200 include a method of assembling the RICC assembly 100 or 200 and a method of using the RICC assembly 100 or 200.

Figure 8:
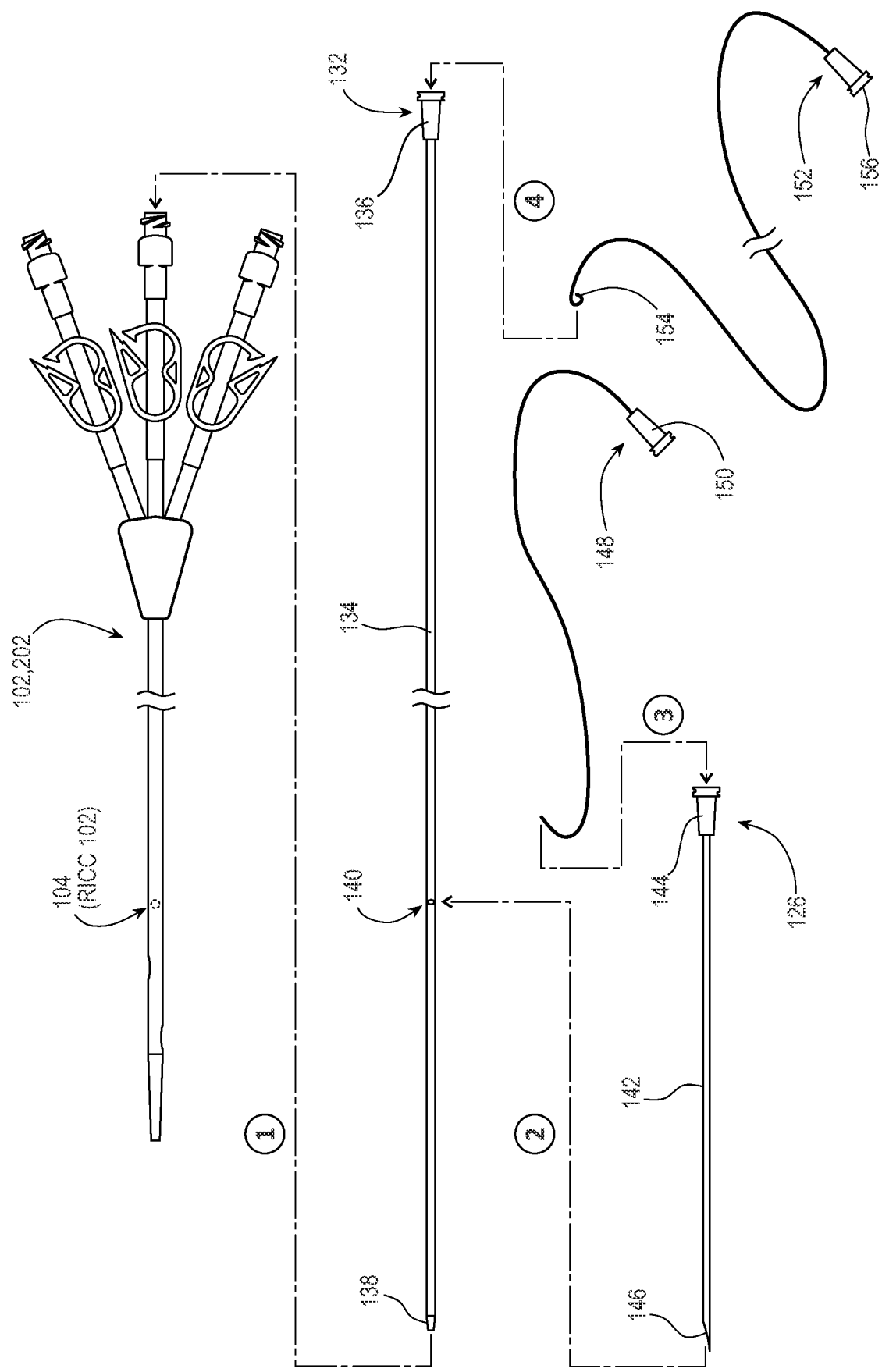
FIG. 8 illustrates a method of assembling the RICC assembly of FIG. 1 or 2 in accordance with some embodiments.

As to the method of assembling the RICC assembly 100 or 200, FIG. 8 illustrates the method of assembling the RICC assembly 100 or 200 in accordance with some embodiments.

As shown, the method of assembling the RICC assembly 100 or 200 includes an introducer-catheter insertion step, an introducer-needle insertion step, an access-guidewire insertion step, and a maneuver-guidewire insertion step.

The introducer-catheter insertion step includes inserting the introducer catheter 132 into the primary lumen 108 of the RICC 102 or 202 by way of the opening of the corresponding Luer connector in the proximal end of the RICC 102 or 202. In addition, the introducer-catheter insertion step includes aligning the introducing hole 140 of the hard catheter tube 134 of the introducer catheter 132 with an aperture of the soft catheter tube 120 or 220 of the RICC 102 or 202. For the RICC 102, such aligning includes aligning the introducing hole 140 of the hard catheter tube 134 with the introducing aperture 104 of the soft catheter tube 120. For the RICC 202, such aligning includes aligning the introducing hole 140 of the hard catheter tube 134 with the secondary-lumen aperture 116 or the tertiary-lumen aperture 118 of the soft catheter tube 220. Lastly, the introducer-catheter insertion step includes ensuring the distal end of the introducer catheter 132 extends at least about 1-7 cm beyond the distal end of the RICC 102 or 202.

The introducer-needle insertion step includes inserting the introducer needle 126 into the single lumen of the introducer catheter 132 by way of the introducing hole 140 of the hard catheter tube 134, thereby locking the introducer and the RICC 102 or 202 together. For the RICC 102, the introducer-needle insertion step includes inserting the introducer needle 126 into the introducing aperture 104 of the soft catheter tube 120, then inserting the introducer needle 126 into the introducing hole 140 of the hard catheter tube 134. For the RICC 202, the introducer-needle insertion step includes inserting the introducer needle 126 into either the secondary-lumen aperture 116 or the tertiary-lumen aperture 118, then piercing the septum 128 between the secondary lumen 110 or the tertiary lumen 112 and the primary lumen 108 of the soft catheter tube 220, and finally inserting the introducer needle 126 into the introducing hole 140 of the hard catheter tube 134 disposed in the primary lumen 108. Lastly, the introducer-needle insertion step includes ensuring the beveled tip 146 of the introducer needle 126 extends past the distal end of the introducer catheter 132.

The access-guidewire insertion step includes inserting the access guidewire 148 into the introducer needle 126 by way of an opening of the introducer-needle hub 144 in a proximal end of the introducer needle 126. In addition, the access-guidewire insertion step includes positioning the access guidewire 148 in the introducer needle 126 such that the distal end of the access guidewire 148 is proximal of the beveled tip 146 of the introducer needle 126 but distal of the distal end of the RICC 102 or 202. Again, such a position for the access guidewire 148 allows for immediate advancement of the distal end of the access guidewire 148 beyond the beveled tip 146 of introducer needle 126 and into a blood-vessel lumen upon establishing access thereto.

The maneuver-guidewire insertion step includes inserting the maneuver guidewire 152 into the introducer catheter 132 by way of an opening of the introducer-catheter hub 136 in a proximal end of the introducer catheter 132. In addition, the maneuver-guidewire insertion step includes positioning the maneuver guidewire 152 in the introducer catheter 132 such that the distal end of the maneuver guidewire 152 is proximal of the introducing hole 140 but distal of the catheter hub 122. Again, such a position for the maneuver guidewire 152 allows for immediate advancement of the distal end of the maneuver guidewire 152 into the blood-vessel lumen upon removing the introducer needle 126 or the shaft 142 thereof from the single lumen of the introducer catheter 132.

As to the method of using the RICC assembly 100 or 200, the method of using the RICC assembly 100 or 200 includes an RICC assembly-obtaining step, a needle tract-establishing step, an access guidewire-advancing step, and an introducer needle-withdrawing step.

The RICC assembly-obtaining step includes obtaining the RICC assembly 100 or 200 including the RICC 102 or 202 and the introducer 106. As set forth above with respect to the ready-to-deploy state of the RICC assembly 100 or 200, the introducer 106 includes the introducer catheter 132 disposed in the primary lumen 108 of the RICC 102 or 202 such that the distal-end portion of the introducer catheter 132 extends past the distal end of the RICC 102 or 202.

The method can further include an ensuring step of ensuring the distal end of the introducer catheter 132 extends at least about 1-7 cm beyond the distal end of the RICC 102 or 202 before performing the needle tract-establishing step.

The needle tract-establishing step includes establishing a needle tract from an area of skin to a blood-vessel lumen of a patient with the beveled tip 146 of the introducer needle 126 of the introducer 106. As set forth above with respect to the ready-to-deploy state of the RICC assembly 100 or 200, the introducer needle 126 extends through the side of the soft catheter tube 120 or 220 of the RICC 102 or 202, through the side of the hard catheter tube 134 of the introducer catheter 132, and out the distal end of the introducer catheter 132.

The access guidewire-advancing step includes advancing the access guidewire 148 through the introducer needle 126 and into the blood-vessel lumen of the patient.

The method can further include a first RICC-advancing step of advancing the distal-end portion of the introducer catheter 132 into the blood-vessel lumen over the access guidewire 148.

The introducer needle-withdrawing step includes withdrawing the introducer needle 126 from both the blood-vessel lumen and the RICC assembly 100 or 200 leaving the access guidewire 148 and the introducer catheter 132 in the blood-vessel lumen.

The method can further include a maneuver guidewire 152-advancing step of advancing the maneuver guidewire 152 through the introducer catheter 132 and into the blood-vessel lumen. However, the maneuver guidewire 152-advancing step requires first withdrawing the introducer needle 126 from both the blood-vessel lumen and the RICC assembly 100 or 200.

The method can further include a second RICC-advancing step of advancing both the distal-end portion of the introducer catheter 132 and a distal-end portion of the RICC 102 or 202 farther into the blood-vessel lumen over the maneuver guidewire 152 such as to the SVC.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") assembly, comprising:
   a RICC including:
      a soft catheter tube having an introducing aperture through a side of the soft catheter tube in a distal-end portion thereof, the introducing aperture opening into an introducing portion of a primary lumen of the RICC that extends from the introducing aperture to a distal end of the RICC;
      a catheter hub coupled to a proximal-end portion of the soft catheter tube; and
      one or more extension legs, each extension leg of the one-or-more extension legs coupled to the catheter hub by a distal-end portion thereof; and
   an introducer including:
      an introducer catheter including a hard catheter tube having an introducing hole through a side of the hard catheter tube in a distal-end portion thereof, the introducing hole opening into an introducing portion of a single lumen of the introducer catheter that extends from the introducing hole to a distal end of the introducer catheter; and
      an introducer needle, the introducer catheter disposed in the primary lumen of the RICC such that the distal end of the introducer catheter extends past the distal end of the RICC and the introducer needle disposed in the introducer catheter through both the introducing aperture and the introducing hole such that a beveled tip in a distal-end portion of the introducer needle extends past the distal end of the introducer catheter when the RICC assembly is in a ready-to-deploy state thereof.

2. The RICC assembly of claim 1, further comprising an access guidewire disposed in the introducer needle such that a distal end of the access guidewire is proximal of the beveled tip but distal of the distal end of the RICC when the RICC assembly is in the ready-to-deploy state.

3. The RICC assembly of claim 2, wherein the access guidewire includes a stop about a proximal-end portion of the access guidewire forming a stop end thereof, the stop end of the access guidewire configured to provide a distal limit for advancing the access guidewire into the RICC.

4. The RICC assembly of claim 1, further comprising a maneuver guidewire disposed in the introducer catheter such that a distal end of the maneuver guidewire is proximal of the introducing hole but distal of the catheter hub when the RICC assembly is in the ready-to-deploy state.

5. The RICC assembly of claim 4, wherein the maneuver guidewire includes a stop about a proximal-end portion of the maneuver guidewire forming a stop end thereof, the stop end of the maneuver guidewire configured to provide a distal limit for advancing the maneuver guidewire into the RICC.

6. The RICC assembly of claim 1, wherein the soft catheter tube is formed of a first material having a first durometer and the hard catheter tube is formed of a second material having a second durometer greater than the first durometer, thereby providing the RICC assembly a column strength for advancing the RICC into a blood-vessel lumen over a guidewire.

7. The RICC assembly of claim 1, wherein the RICC includes a set of three lumens including the primary lumen, a secondary lumen, and a tertiary lumen formed of fluidly connected portions of three catheter-tube lumens, three hub lumens, and three extension-leg lumens.

8. The RICC assembly of claim 7, wherein the primary lumen has a primary-lumen aperture in the distal end of the RICC, the secondary lumen has a secondary-lumen aperture in the side of the soft catheter tube proximal of the primary-lumen aperture, and the tertiary lumen has a tertiary-lumen aperture in the side of the soft catheter tube proximal of the secondary-lumen aperture but distal of the introducing aperture.

9. A rapidly insertable central catheter ("RICC") assembly, comprising:
a RICC including:
a soft catheter tube having a primary-lumen aperture in a distal end of the soft catheter tube and a secondary-lumen aperture in a side of the soft catheter tube in a distal-end portion thereof;
a catheter hub coupled to a proximal-end portion of the soft catheter tube; and
one or more extension legs, each extension leg of the one-or-more extension legs coupled to the catheter hub by a distal-end portion thereof; and
an introducer including:
an introducer catheter including a hard catheter tube having an introducing hole through a side of the hard catheter tube in a distal-end portion thereof; and
an introducer needle, the introducer catheter disposed in a primary lumen of the RICC such that a distal end of the introducer catheter extends past a distal end of the RICC and the introducer needle disposed in the introducer catheter through a combination of the secondary-lumen aperture, a septum dividing a secondary lumen from the primary lumen, and the introducing hole such that a beveled tip in a distal-end portion of the introducer needle extends past the distal end of the introducer catheter when the RICC assembly is in a ready-to-deploy state thereof.

10. The RICC assembly of claim 9, further comprising an access guidewire disposed in the introducer needle such that a distal end of the access guidewire is proximal of the beveled tip but distal of the distal end of the RICC when the RICC assembly is in the ready-to-deploy state.

11. The RICC assembly of claim 10, wherein the access guidewire includes a stop about a proximal-end portion of the access guidewire forming a stop end thereof, the stop end of the access guidewire configured to provide a distal limit for advancing the access guidewire into the RICC.

12. The RICC assembly of claim 9, further comprising a maneuver guidewire disposed in the introducer catheter such that a distal end of the maneuver guidewire is proximal of the introducing hole but distal of the catheter hub when the RICC assembly is in the ready-to-deploy state.

13. The RICC assembly of claim 12, wherein the maneuver guidewire includes a stop about a proximal-end portion of the maneuver guidewire forming a stop end thereof, the stop end of the maneuver guidewire configured to provide a distal limit for advancing the maneuver guidewire into the RICC.

14. The RICC assembly of claim 9, wherein the soft catheter tube is formed of a first material having a first durometer and the hard catheter tube is formed of a second material having a second durometer greater than the first durometer, thereby providing the RICC assembly a column strength for advancing the RICC into a blood-vessel lumen over a guidewire.

15. The RICC assembly of claim 9, wherein the RICC includes a set of three lumens including the primary lumen, the secondary lumen, and a tertiary lumen formed of fluidly connected portions of three catheter-tube lumens, three hub lumens, and three extension-leg lumens.

16. The RICC assembly of claim 15, wherein the primary lumen has the primary-lumen aperture in the distal end of the RICC, the secondary lumen has the secondary-lumen aperture in the side of the soft catheter tube proximal of the primary-lumen aperture, and the tertiary lumen has a tertiary-lumen aperture in the side of the soft catheter tube proximal of the secondary-lumen aperture.

* * * * *